United States Patent [19]
Horwell et al.

[11] Patent Number: 6,020,370
[45] Date of Patent: Feb. 1, 2000

[54] BRIDGED CYCLIC AMINO ACIDS AS PHARMACEUTICAL AGENTS

[75] Inventors: David Christopher Horwell, Foxton; Justin S. Bryans, Balsham; Clare O. Kneen, Little Walden; Andrew I. Morrell, Huntingdon; Giles S. Ratcliffe, Near Royston, all of United Kingdom

[73] Assignee: Warner-Lambert Company, Morris Plains, N.J.

[21] Appl. No.: 09/068,861

[22] PCT Filed: Feb. 18, 1997

[86] PCT No.: PCT/US97/02401

§ 371 Date: May 19, 1998

§ 102(e) Date: May 19, 1998

[87] PCT Pub. No.: WO97/33859

PCT Pub. Date: Sep. 18, 1997

Related U.S. Application Data

[60] Provisional application No. 60/013,433, Mar. 14, 1996.

[51] Int. Cl.⁷ ..................... A61K 31/215; C07C 69/74; C07C 61/12
[52] U.S. Cl. .................. 514/511; 514/561; 560/117; 560/118; 560/120; 560/122; 560/125; 562/499; 562/500; 562/502; 562/504; 562/507
[58] Field of Search .................... 562/507, 499, 562/500, 502, 504; 514/561, 511; 560/117, 118, 120, 125, 122

[56] References Cited

U.S. PATENT DOCUMENTS

| | | | |
|---|---|---|---|
| 3,641,129 | 2/1972 | Loeffler et al. | 562/500 |
| 3,743,742 | 7/1973 | Loeffler et al. | 424/319 |
| 4,024,175 | 5/1977 | Satzinger et al. | 260/468 J |
| 4,087,544 | 5/1978 | Satzinger et al. | 424/305 |

FOREIGN PATENT DOCUMENTS

| | | |
|---|---|---|
| 2029807 | of 0000 | Germany . |
| 2543821 | of 0000 | Germany . |
| 2551728 | of 0000 | Germany . |

OTHER PUBLICATIONS

Loeffler et al., Bridged . . . Process, J. of Medicinal Chemistry, vol. 13, No. 5, pp. 926–935, Sep. 1970.
PCT International Search Report, PCT/US97/02401.
Mann et al., Chemical Abstracts, vol. 114, No. 19, 1991, abstract No. 184942k.

*Primary Examiner*—Rasalynd Keys
*Attorney, Agent, or Firm*—Elizabeth M. Anderson

[57] ABSTRACT

Bridged cyclic amino acids of formula

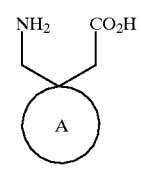

I are disclosed and are useful as agents in the treatment of epilepsy, faintness attacks, hypokinesia, cranial disorders, neurodegenerative disorders, depression, anxiety, panic, pain and neuropathological disorders. Processes for the preparation and intermediates useful in the preparation are also disclosed.

24 Claims, No Drawings

BRIDGED CYCLIC AMINO ACIDS AS PHARMACEUTICAL AGENTS

This application claims the benefit of U.S. Provisional Application No. 60/013,433, filed Mar. 14, 1996.

BACKGROUND OF THE INVENTION

Compounds of formula

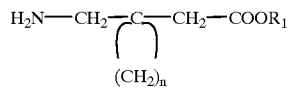

wherein $R_1$ is hydrogen or a lower alkyl radical and n is 4, 5, or 6 are known in U.S. Pat. No. 4,024,175 and its divisional U.S. Pat. No. 4,087,544. The uses disclosed are: protective effect against cramp induced by thiosemicarbazide; protective action against cardiazole cramp; the cerebral diseases, epilepsy, faintness attacks, hypokinesia, and cranial traumas; and improvement in cerebral functions. The compounds are useful in geriatric patients. The patents are hereby incorporated by reference.

SUMMARY OF THE INVENTION

The novel bridged cyclic amino acids, their derivatives, pharmaceutically acceptable salts, and prodrugs are useful in a variety of disorders. The disorders include: epilepsy, faintness attacks, hypokinesia, cranial disorders, neurodegenerative disorders, depression, anxiety, panic, pain, and neuropathological disorders.

The compounds are those of formula

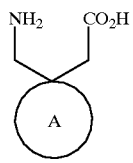

I a pharmaceutically acceptable salt thereof or a prodrug thereof wherein A is a bridged ring selected from

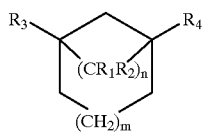

(1)

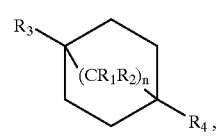

(2)

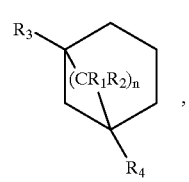

(3)

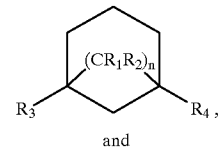

(4)

and

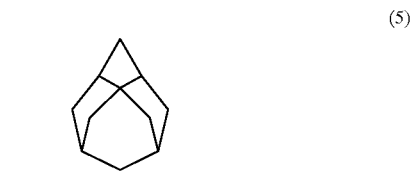

(5)

wherein $R_1$ and $R_2$ are each independently selected from hydrogen and methyl;

$R_3$ and $R_4$ are each independently selected from hydrogen or methyl;

n is an integer of from 1 to 4; and m is an integer of from 0 to 2.

Preferred compounds are those of Formula I wherein

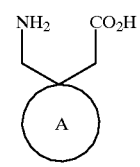

I or a pharmaceutically acceptable salt thereof wherein A is a bridged ring selected from

(1)

(2)

(3)

(4)

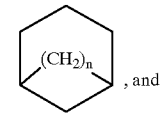

, and

-continued

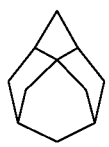
(5)

wherein
n is an integer of from 1 to 4; and
m is an integer of from 0 to 2.

Other preferred compounds are, for example, (2-Aminomethyl-bicyclo[2.2.1]hept-2-yl)-acetic acid methyl ester monohydrochloride, [2-(Acetylamino-methyl)-bicyclo[2.2.1]hept-2-yl]-acetic acid, and [2-(2-Aminomethyl-bicyclo[2.2.1]hept-2-yl)-acetylamino]-acetic acid monohydrochloride.

Novel intermediates useful in the preparation of the final products are disclosed as well as a novel process for the preparation of the compounds.

DETAILED DESCRIPTION

The compounds of the instant invention and their pharmaceutically acceptable salts are as defined by Formula I.

The term "alkyl" is a straight or branched group of from 1 to 6 carbon atoms including but not limited to methyl, ethyl, propyl, n-propyl, isopropyl, butyl, 2-butyl, tert-butyl, pentyl, hexyl, and n-hexyl.

The benzyl and phenyl groups may be unsubstituted or substituted by from 1 to 3 substituents selected from halogen, $CF_3$, nitro, alkyl, alkoxy.

Since amino acids are amphoteric, pharmacologically compatible salts when R is hydrogen can be salts of appropriate inorganic or organic acids, for example, hydrochloric, sulphuric, phosphoric, acetic, oxalic, lactic, citric, malic, salicylic, malonic, maleic, succinic, and ascorbic. Starting from corresponding hydroxides or carbonates, salts with alkali metals or alkaline earit metals, for example, sodium, potassium, magnesium, or calcium are formed. Salts with quaternary ammonium ions can also be prepared with, for example, the tetramethyl-ammonium ion. The carboxyl group of the amino acids can be esterified by known means.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof. In all cases where there is a chiral center at the point where the amino methyl and acetic acid moieties are joined to the ring, the center may have either the R or S configuration.

The compounds of the invention may be synthesized, for example, by utilizing the general strategy (Scheme 1 below) outlined by Griffiths G., et al., Helv. Chim. Acta, 74:309 (1991). Alternatively, they may also be made as shown (in Scheme 2 below), analogously to the published procedure for the synthesis of 3-oxo-2,8-diazaspiro[4,5]decane-8-carboxylic acid tert-butyl ester (1) (Smith P. W., et al., J. Med. Chem., 38:3772 (1995)). The compounds may also be synthesized by the methods outlined by Satzinger G., et al., (U.S. Pat. Nos. 4,024,175, and 4,152,326) (Schemes 3 and 4 below).

The compounds may be synthesized by utilizing the general strategy exemplified by the synthesis of compounds of formula (1) outlined by G. Griffiths, et al., (Helv. Chim. Acta, 74;309 (1991)). See Scheme 1 below.

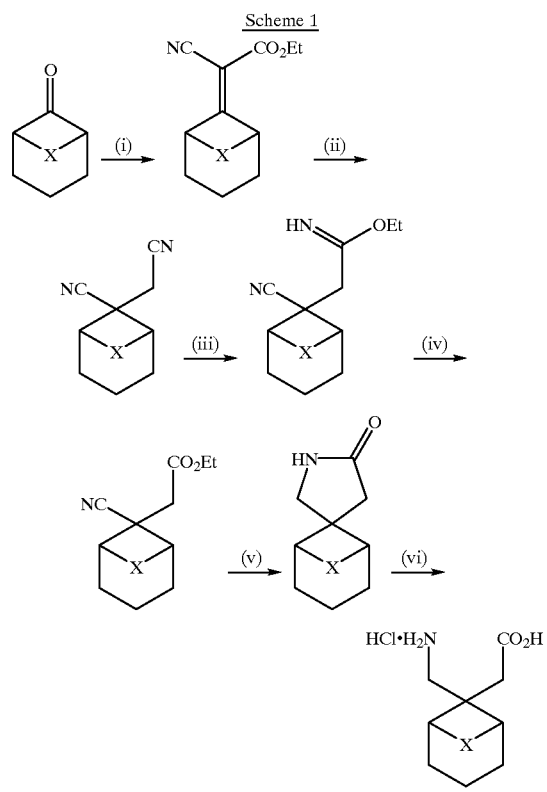

(i) Ethyl cyanoacetate, piperidine (Cope, et al., J. Am. Chem. Soc., 63:3452 (1941))
(ii) NaCN, EtOH/$H_2O$,
(iii) EtOH, HCl,
(iv) $H_2O/H^+$,
(v) $H_2$, Rh/C, MeOH,
(vi) HCl Alternatively, the compounds of the invention may be made as shown in Scheme 2 below, analogously to the published procedure for the synthesis of 3-oxo-2,8-diazaspiro[4,5]decane-8-carboxylic acid tert-butyl ester (6) (P. W. Smith, et al., J. Med. Chem., 38;3772 (1995)).

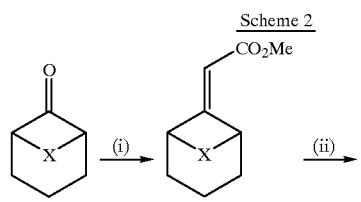

-continued

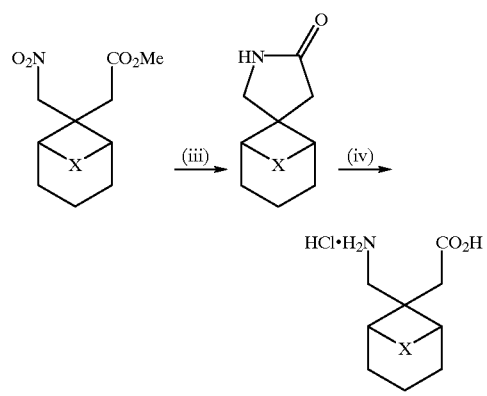

(i) Ph$_3$P = CHCO$_2$Me,
(ii) MeNO$_2$, 1,1,3,3-tetramethylguanidine,
(iii) Raney nickle, EtOH/H$_2$O
(iv) HCl The compounds may also be synthesized by the methods outlined-by G. Satzinger, et al., (U.S. Pat. Nos. 4,024,175, and 4,152,326). See Schemes 3 and 4 below.

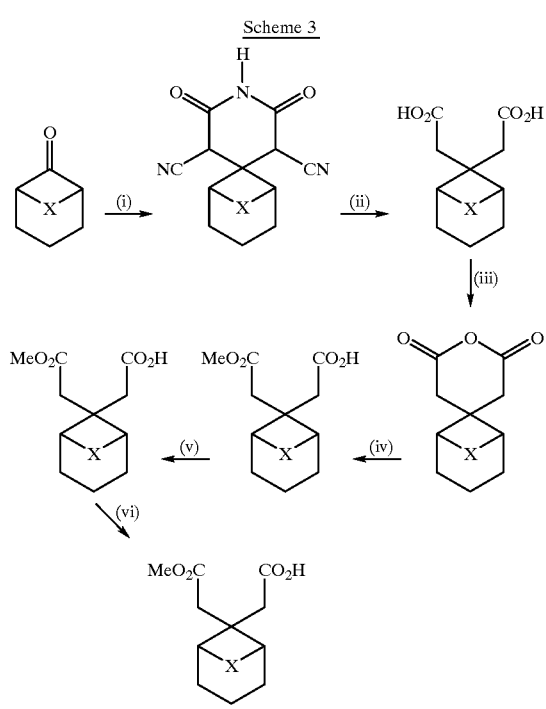

(i) Ethylcyanoacetate, ammonia then H$_3$O$^+$;
(ii) H$_2$SO$_4$;
(iii) Ac$_2$O;
(iv) MeOH;
(v) Curtius Reaction;
(vi) HCl, H$_2$O then anion exchange

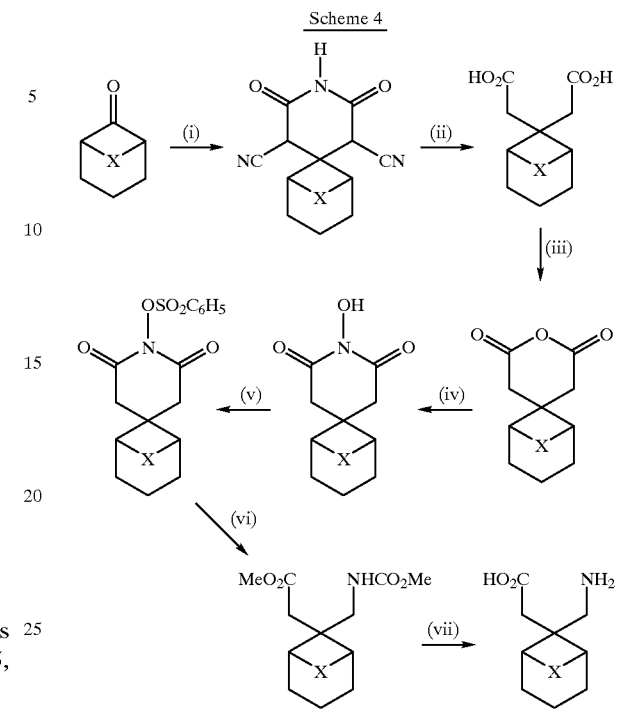

(i) Ethylcyanoacetate, amonia then H$_3$O$^+$;
(ii) H$_2$SO$_4$;
(iii) Ac$_2$O;
(iv) H$_2$NOH;
(v) PhSO$_2$Cl;
(vi) Et$_3$N, MeOH;
(vii) HCl, H$_2$O then anion exchange When X is —(CH$_2$)$_2$— and Z is NR and R is C(O)R1 or CO$_2$R$^2$, except where R$^2$ is a benzyl group, the compounds may be synthesized by the route outlined by G. Griffiths, et al., (*Helv. Chim. Acta,* 74;309 (1991)). See Scheme 5 below.

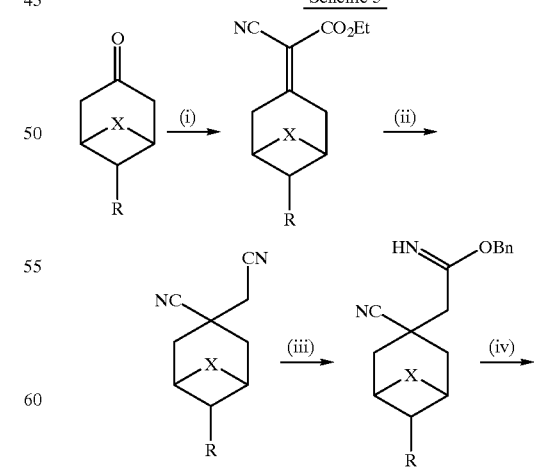

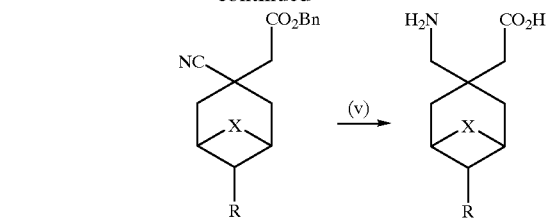

(i) Ethyl cyanoacetate, piperidine (Cope, et al., J. Am. Chem. Soc., 63:3452 (1941));
(ii) NaCN, EtOH/H$_2$O;
(iii) BnOH, HCl;
(iv) H$_2$O/H$^+$;
(v) H$_2$, Rh/C, MeOH Examples of pro-drugs are:

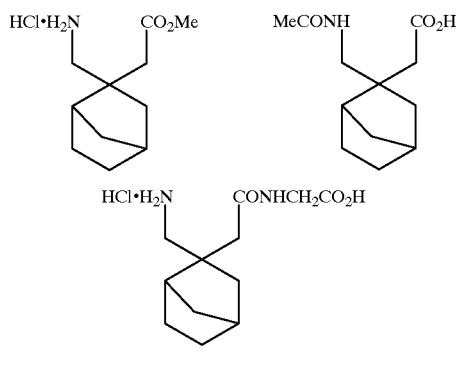

These can be synthesised, for example, via Schemes 6 to 8.

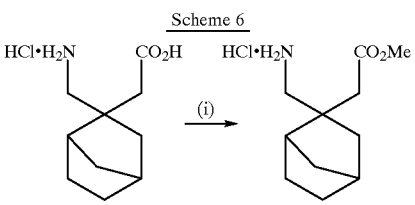

(i) MeOH, HCl reflux

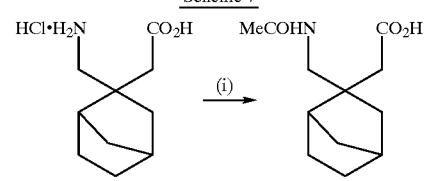

(i) MeCOCl, NaOH, H$_2$O

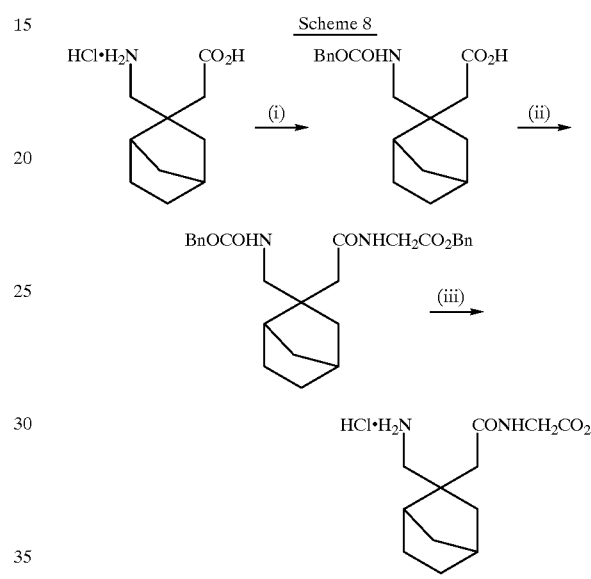

(i) BnOCOCl, H$_2$O, 1,4-dioxan, NaOH
(ii) (a) Dicyclohexylcarbodiimide pentafluorophenol, Ethyl acetate
    (b) glycine benzyl ester, triethylamine
(iii) Pd(OH)$_2$/C, HCl, EtOH, H$_2$ The radioligand binding assay using [$^3$H]gabapentin and the α$_2$δ subunit derived from porcine brain tissue was used ("The Novel Anti-convulsant Drug, Gabapentin, Binds to the α$_2$δ Subunit of a Calcium Channel", Gee N., et al., *J. Biological Chemistry*, in press).

TABLE 1

| Compound | IC$_{50}$ (μM) | Number |
|---|---|---|
| 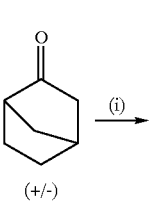 | 0.103 | 5 |

TABLE 1-continued

| Compound | IC$_{50}$ (μM) | Number |
|---|---|---|
| 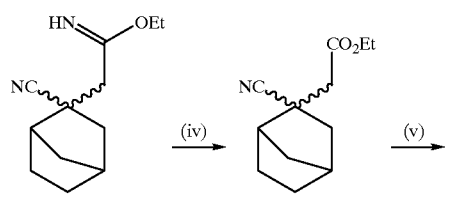 | | |
| 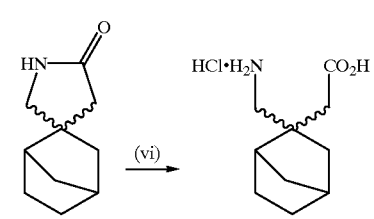 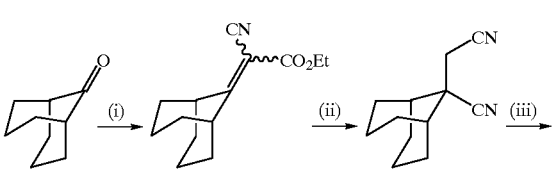 | 0.047 | 3 |
| 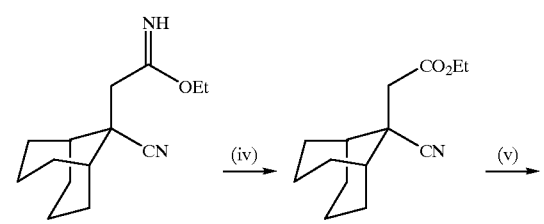 | | |
| 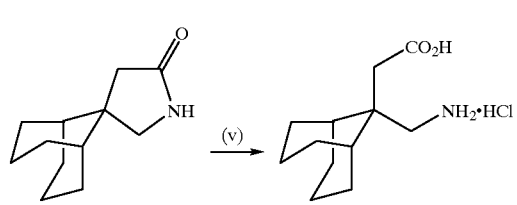 | | |

Table 1 above shows the binding affinity of the examples to the α$_2$δ subunit. Gabapentin (Neurontin®) is about 0.10 to 0.12 μM in this assay. The compounds of the instant invention are expected, therefore, to exhibit pharmacologic properties comparable to gabapentin. For example, as agents for convulsions, anxiety, and pain.

The compounds of the invention are related to Neurontin®, a marketed drug effective in the treatment of epilepsy. Neurontin® is 1-(aminomethyl)cyclohexaneacetic acid of structural formula

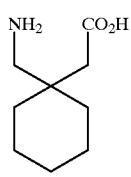

The compounds of the invention are also expected to be useful in the treatment of epilepsy. See Table 1 above for IC$_{50}$ data as compared to Neurontin®.

The present invention also relates to therapeutic use of the compounds of the mimetic as agents for neurodegenerative disorders.

Such neurodegenerative disorders are, for example, Alzheimer's disease, Huntington's disease, Parkinson's disease, and Amyotrophic Lateral Sclerosis.

The present invention also covers treating neurodegenerative disorders termed acute brain injury. These include but are not limited to: stroke, head trauma, and asphyxia.

Stroke refers to a cerebral vascular disease and may also be referred to as a cerebral vascular incident (CVA) and includes acute thromboembolic stroke. Stroke includes both focal and global ischemia. Also, included are transient cerebral ischemic attacks and other cerebral vascular problems accompanied by cerebral ischemia such as in a patient undergoing carotid endarterectomy specifically or other cerebrovascular or vascular surgical procedures in general, or diagnostic vascular procedures including cerebral angiography and the like.

Other incidents are head trauma, spinal cord trauma, or injury from general anoxia, hypoxia, hypoglycemia, hypotension as well as similar injuries seen during procedures from embole, hyperfusion, and hypoxia.

The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

GABA is an inhibitory neurotransmitter with the central nervous system. Within the general context of inhibition, it seems likely that GABA-mimetics might decrease or inhibit cerebral function and might therefore slow function and decrease mood leading to depression.

The compounds of the instant invention may produce an anticonvulsant effect through the increase of newly created GABA at the synaptic junction. If gabapentin does indeed increase GABA levels or the effectiveness of GABA at the synaptic junction, then it could be classified as a GABA-mimetic and might decrease or inhibit cerebral function and might, therefore, slow function and decrease mood leading to depression.

The fact that a GABA agonist or GABA-mimetic might work just the opposite way by increasing mood and thus, be an antidepressant, is a new concept, different from the prevailing opinion of GABA activity heretofore.

The compounds of the instant invention are also expected to be useful in the treatment of anxiety and of panic as demonstrated by means of standard pharmacological procedures.

MATERIAL AND METHODS

Carrageenin-induced Hyperalgesia

Nociceptive pressure thresholds were measured in the rat paw pressure test using an analgesymeter (Randall-Selitto Method: Randall L. O., Sellitto J. J., A method for measurement of analgesic activity on inflamed tissue. Arch. Int. Pharmacodyn., 4:409–419 (1957)). Male Sprague Dawley rats (70–90 g) were trained on this apparatus before the test day. Pressure was gradually applied to the hind paw of each rat and nociceptive thresholds were determined as the pressure (g) required to elicit paw withdrawal. A cutoff point of 250 g was used to prevent any tissue to the paw. On the test day, two to three baseline measurements were taken before animals were administered 100 µL of 2% carrageenin by intraplantar injection into the right hind paw. Nociceptive thresholds were taken again 3 hours after carrageenin to establish that animals were exhibiting hyperalgesia. Animals were dosed with either gabapentin (3–300 mg/kg, s.c.), morphine (3 mg/kg, s.c.), or saline at 3.5 hours after carrageenin and nociceptive thresholds were examined at 4, 4.5, and 5 hours post carrageenin.

Semicarbazide-induced Tonic Seizures

Tonic seizures in mice are induced by subcutaneous administration of semicarbazide (750 mg/kg). The latency to the tonic extension of forepaws is noted. Any mice not convulsing within 2.0 hours after semicarbazide are considered protected and given a maximum latency score of 120 minutes.

Animals

Male Hooded Lister rats (200–250 g) are obtained from Interfauna (Huntingdon, UK) and male TO mice (20–25 g) are obtained from Bantin and Kingman (Hull, UK). Both rodent species are housed in groups of six. Ten Common Marmosets (Callithrix Jacchus) weighing between 280 and 360 g, bred at Manchester University Medical School (Manchester, UK) are housed in pairs. All animals are housed under a 12-hour light/dark cycle (lights on at 07.00 hour) and with food and water ad libitum.

Drug Administration

Drugs are administered either intraperitoneally (IP) or subcutaneously (SC) 40 minutes before the test in a volume of 1 mL/kg for rats and marmosets and 10 mL/kg for mice.

Mouse Light/Dark Box

The apparatus is an open-topped box, 45 cm long, 27 cm wide, and 27 cm high, divided into a small (2/5) and a large (3/5) area by a partition that extended 20 cm above the walls (Costall B., et al., Exploration of mice in a black and white box: validation as a model of anxiety. Pharmacol. Biochem. Behav., 32:777–785 (1989)).

There is a 7.5×7.5 cm opening in the center of the partition at floor level. The small compartment is painted black and the large compartment white. The white compartment is illuminated by a 60-W tungsten bulb. The laboratory is illuminated by red light. Each mouse is tested by placing it in the center of the white area and allowing it to explore the novel environment for 5 minutes. The time spent in the illuminated side is measured (Kilfoil T., et al., Effects of anxiolytic and anxiogenic drugs on exploratory activity in a simple model of anxiety in mice. Neuropharmacol., 28:901–905 (1989)).

Rat Elevated X-Maze

A standard elevated X-maze (Handley S. L., et al., Effects of alpha-adrenoceptor agonists and antagonists in a maze-exploration model of 'fear'-motivated behavior. Naunyn-Schiedeberg's Arch. Pharmacol., 327:1–5 (1984)), was automated as previously described (Field, et al., Automation of the rat elevated X-maze test of anxiety. Br. J. Pharmacol., 102(Suppl):304P (1991)). The animals are placed on the center of the X-maze facing one of the open arms. For determining anxiolytic effects the entries and time spent on the end half sections of the open arms is measured during the 5-minute test period (Costall, et al., Use of the elevated plus maze to assess anxiolytic potential in the rat. Br. J. Pharmacol., 96(Suppl):312P (1989)).

Marmoset Human Threat Test

The total number of body postures exhibited by the animal towards the threat stimulus (a human standing approximately 0.5 m away from the marmoset cage and staring into the eyes of the marmoset) is recorded during the 2-minute test period. The body postures scored are slit stares, tail postures, scent marking of the cage/perches, piloerection, retreats, and arching of the back. Each animal is exposed to the threat stimulus twice on the test day before and after drug treatment. The difference between the two scores is analyzed using one-way analysis of variance followed by Dunnett's t-test. All drug treatments are carried out SC at least 2 hours after the first (control) threat. The pretreatment time for each compound is 40 minutes.

Rat Conflict Test

Rats are trained to press levers for food reward in operant chambers. The schedule consists of alternations of four 4-minute unpunished periods on variable interval of 30 seconds signalled by chamber lights on and three 3-minute punished periods on fixed ratio 5 (by footshock concomitant to food delivery) signalled by chamber lights off. The degree of footshock is adjusted for each rat to obtain approximately 80% to 90% suppression of responding in comparison with unpunished responding. Rats receive saline vehicle on training days.

The compounds of the instant invention are also expected to be useful in the treatment of pain and phobic disorders (Am. J. Pain Manag., 5:7–9 (1995)).

The compounds of the instant invention are also expected to be useful in treating the symptoms of manic, acute or chronic, single upside, or recurring. They are also expected to be useful in treating and/or preventing bipolar disorder (U.S. patent application Ser. No. 08/440,570 filed May 15, 1995).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following examples are illustrative of the instant invention; they are not intended to limit the scope.

General Method Exemplified by the Synthesis of Bicyclic [3,3,1] Nonane Gabapentin

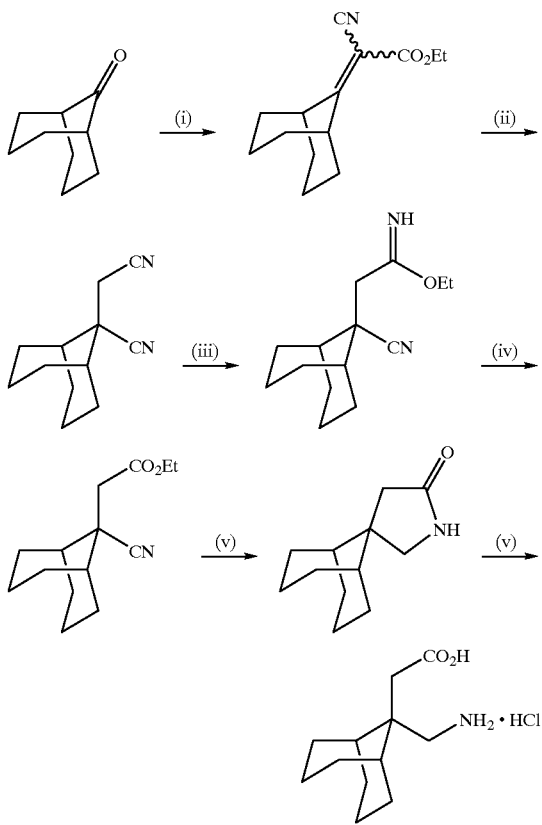

(i) EtO$_2$CCH$_2$CN, NH$_4$Ac, AcOH, toluene, 120° C.,
(ii) a. NaCN, EtOH (95%), H$_2$O, 115° C.
    b. HCl (g),
(iii) EtOH, HCl, (g), toluene,
(iv) HCl, H$_2$O,
(v) H$_2$, EtOH/NH$_3$, Raney nickel, 30–50° C.,
(vi) HCl, H$_2$O, 140° C.

STEP 1

Cyanoacetate

Bicyclo[3,3,1]nonan-9-one (15.7 mmol), ethyl cyanoacetate (15.7 mmol), ammonium acetate (3.1 mmol), glacial acetic acid (12.5 mmol), and toluene (30 mL) were combined and heated to reflux under nitrogen with azeotropic removal of water via a Dean-Stark trap. After 24 hours, the mixture was cooled to-room temperature and left to stand for a further 24 hours. The mixture was then washed with water (3×30 mL) and the water washes combined and extracted with toluene (3×30 mL). The original organic phase and the organic washes were combined, dried (MgSO$_4$), and the solvent removed in vacuo to give 3.58 g (98%) of a clear oil which crystallized on standing.

$^1$H NMR (CDCl$_3$) 400 MHz: δ 1.35 (3H, t, J=7.2 Hz), 1.53–1.60 (3H, m), 1.80–2.20 (10H, m), 3.20 (1H, Br s), 4.15 (1H, Br s), 4.27 (2H, q, J=7.2 Hz).

MS (CI) m/z: 95, 121, 160, 188, 205, 206, 233, 234 (100% MH$^+$), 235, 251, 262.

IR (CH$_2$Cl$_2$) υ$_{max}$ cm$^{-1}$: 2926, 2853, 2224, 1727, 1593, 1447, 1369, 1290, 1262, 1232, 1216, 1123, 1076, 1023, 963, 903, 782.

Microanalysis: C$_{14}$H$_{12}$NO$_2$.0.04 H$_2$O: Calc'd: C, 71,85; H, 8.22; N, 5.98. Found: C, 71.61; H, 8.19; N, 5.94.

STEP 2

Binitrile

The cyanoacetate (4 mmol) and NaCN (4 mmol) were dissolved in a mixture of ethanol (15 mL) and water (0.6 mL) and heated to reflux. After 24 hours, the solution was cooled to room temperature and filtered. The filtrate was acidified by passing HCl gas through the solution. The mixture was then filtered again. The filtrate was evaporated to dryness in vacuo to leave 0.64 g (85%) of a white waxy solid. Recrystallization from ethanol/heptane gave white needles, mp 120–125° C.

$^1$H NMR (CDCl$_3$) 400 MHz: δ 1.50–2.35 (14H, m), 2.92 (2H, s).

MS (CI) m/z: 121, 162, 189 (100% MH$^+$) 290, 217.

IR (CH$_2$Cl$_2$)υ$_{max}$ cm$^{-1}$: 2954, 2933, 2913, 2865, 2244, 2228, 1491, 1464, 1441, 1423, 1230, 1124, 897, 872.

Microanalysis: C$_{12}$H$_{16}$NO$_2$.0.2 H$_2$O: Calc'd: C, 75,12; H, 8.51; N, 14.60. Found: C, 75.12; H, 8.56; N, 14.61.

STEP 3

Imidate

The binitrile (10 mmol) was dissolved in a mixture of ethanol (50 mL) and toluene (20 mL) and cooled to 0° C. in an ice bath. The mixture was then saturated with HCl gas. The flask was stoppered and the mixture left to stand at room temperature. After 60 hours, the solvent was removed in vacuo. The residue was triturated with diethyl ether to give 1.97 g (70%) of a white powder, mp 190–210° C.

$^1$H NMR (DMSO) 400 MHz: δ 1.36 (3H, t, J=7.2 Hz), 1.40–1.61 (4H, m), 1.75–1.80 (3H, m), 1.83–1.94 (5H, m), 2.03–2.08 (2H, m), 3.34 (2H, s), 4.51 (2H, q, J=7.2 Hz).

MS (CI) m/z: 121, 189, 190, 222, 235 (100% MH$^+$), 236.

IR (MeOH) υ$_{max}$ cm$^{-1}$: 3383, 2924, 2894, 2867, 2233, 1645, 1574, 1456, 1394, 1243, 1142, 1105, 1006, 952, 835.

Microanalysis: C$_{14}$H$_{22}$N$_2$O.1.0 HCl, 0.5 H$_2$O: Calc'd: C, 59.88; H, 8.61; N, 9.98. Found: C, 60.00; H, 8.49; N, 10.24.

STEP 4

Ester

The imidate (6.7 mmol) was dissolved in water (100 mL) and the pH adjusted to pH 1.5 by addition of 1N HCl. The resulting solution was stirred at room temperature overnight. The solution was then shaken with ethyl acetate (100 mL). The organic phase was separated, washed with water, dried (MgSO$_4$), and the solvent removed in vacuo to give 1.41 g (90%) of a clear oil which crystallized on standing, mp 52–56° C.

$^1$H NMR (CDCl$_3$) 400 MHz: δ 1.29 (3H, t, J=7.2 Hz), 1.57–1.59 (1H, m), 1.62–1.71 (3H, m), 1.75–1.94 (6H, m), 2.10, (2H, Br s), 2.25–2.34 (2H, m), 2.82 (2H, s), 4.21 (2H, q, J=7.2 Hz).

MS (CI) m/z: 121, 162, 190, 209, 235, 236 (100% MH$^+$), 237.

IR (CH$_2$Cl$_2$) υ$_{max}$ cm$^{-1}$: 3439, 2993, 2924, 2863, 2230, 1728, 1475, 1459, 1440, 1411, 1366, 1338, 1216, 1171, 1116, 1031, 948, 876.

Microanalysis: C$_{14}$H$_{21}$NO$_2$: Calc'd: C, 71.46; H, 8.99; N, 5.95. Found: C, 71.69; H, 9.12; N, 6.02.

STEP 5

Lactam

Raney nickel (catalytic) was washed with water (3×30 mL) followed by ethanol (2×30 mL) and added to a solution of the ester (4.5 mmol) in ethanol (40 mL) presaturated with ammonia gas and absolute ethanol (60 mL). The resulting mixture was shaken under an atmosphere of hydrogen gas (50 psi) at 50° C. in a Parr apparatus. After 20 hours, the mixture was filtered through Celite and the filtrate evaporated to dryness in vacuo to give 0.811 g (93%) of a white powder, mp 154–157° C.

$^1$H NMR (CDCl$_3$) 400 MHz: δ 1.49–1.58 (2H, m), 1.63–1.68 (7H, m), 1.76–1.94 (5H, m), 2.37 (2H, s), 3.35 (2H, s), 5.77 (1H, Br s).

MS (CI) m/z: 192, 193, 194 (100% MH$^+$), 195, 208, 222.

IR (CDCl$_3$) υ$_{max}$ cm$^{-1}$: 3419, 3185, 2925, 2864, 1695, 1668, 1489, 1456, 1417, 1353, 1314, 1258, 1222, 1085, 1048, 869, 825.

Microanalysis: C$_{12}$H$_{19}$NO: Calc'd: C, 74.57; H, 9.91; N, 7.25. Found: C, 74.35; H, 10.02; N, 7.05.

STEP 6

Bicyclic [3,3,] nonane gabapentin

The lactam (3.3 mmol) was heated to reflux in a mixture of water (20 mL) and concentrated HCl (20 mL). After 5 days, the mixture was cooled to room temperature and washed with dichloromethane (2×20 mL). The aqueous layer was collected and the solvent removed in vacuo to give 0.123 g (13%) of a pale yellow solid, mp 150–155° C.

$^1$H NMR (DMSO) 400 MHz: δ 1.24–1.66 (8H, m), 1.74–2.16 (6H, m), 2.63 (2H, s), 3.22 (2H, s), 7.90 (3H, Br s), 12.43 (1H, Br s).

MS (CI) m/z: 192, 193, 194 (100% MH$^+$–H$_2$O), 195, 222.

IR (MeOH) υ$_{max}$ cm$^{-1}$: 3419, 3172, 3022, 2934, 1717, 1614, 1509, 1454, 1390, 1321, 1268, 1196.

Microanalysis: C$_{12}$H$_{21}$NO$_2$.1.8 HCl: Calc'd: C, 52.04; H, 8.30; N, 5.06. Found: C, 52.03; H, 8.09; N, 5.09.

EXAMPLE 1

(±) Exo/Endo Bicyclic[(2,2,1]heptane Gabapentin

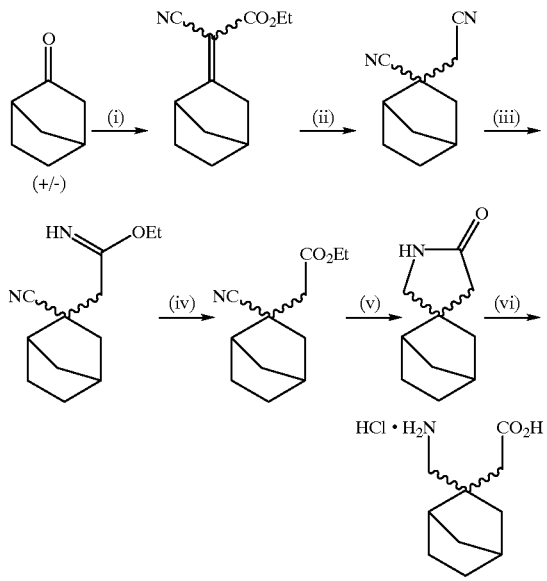

-continued
(i) EtO$_2$CCH$_2$CN, NH$_4$Ac, AcOH, toluene, 120° C.,
(ii) a. NaCN, EtOH (95%), H$_2$O, 115° C.
  b. HCl (g),
(iii) EtOH, HCl, (g), toluene,
(iv) HCl, H$_2$O,
(v) H$_2$, EtOH/NH$_3$, Raney nickel, 30–50° C.,
(vi) HCl, H$_2$O, 140° C.

STEP 1

Cyanoacetate

The ±Norcamphor (80 mmol), ethyl cyanoacetate (80.0 mmol), ammonium acetate (16 mmol), and glacial acetic acid (65 mmol) were reacted as in the General method Step 1 to give a clear oil. Yield 95%. Bpt oven temp 180–200° C.

$^1$H NMR (CDCl$_3$) 400 MHz: δ 1.20–1.40 (4H, m), 1.51 (2H, s), 1.60–1.80 (1H, m), 1.90–2.00 (1H, m), 2.20–2.40 (0.5H, m), 2.50–2.55 (1H, m), 2.67 (1H, s), 3.44 (0.5H, s), 4.20–4.30 (2H, m).

MS (CI) m/z: 133, 149, 159, 160, 177, 178, 180, 206 (100% MH$^+$), 207, 234.

IR (Film) υ$_{max}$ cm$^{-1}$: 2971, 2910, 2879, 2224, 1727, 1621, 1449, 1407, 1368, 1326, 1307, 1289, 1271, 1259, 1231, 1207, 1163, 1137, 1105, 1070, 1028, 964, 921, 857, 775, 747.

Microanalysis: C$_{12}$H$_{15}$NO$_2$: Calc'd: C, 70.22; H, 7.37; N, 6.82. Found: C, 70.24; H, 7.35; N, 6.78.

STEP 2

Binitrile

The cyanoacetate (50 mmol) and NaCN (49 mmol) were reacted as in the General method Step 2 to give a white solid, Yield 98%; mp 44–48° C.

$^1$H NMR (CDCl$_3$) 400 MHz: δ 1.10–1.40 (2H, m), 1.40–1.80 (5H, m), 1.91–1.92 (1H, m), 2.20–2.30 (1H,m), 2.44 (1H, s), 2.58–2.86 (2H,m).

MS (CI) m/z: 93, 134 (100% MH$^+$–C$_2$H$_3$), 161 (MH$^+$), 162, 180.

IR (CH$_2$Cl$_2$) υ$_{max}$ cm$^{-1}$: 2970, 2883, 2235, 1717, 1463, 1447, 1428, 1312, 1278, 1255, 1200, 1151, 1101, 1068, 947, 925, 906, 871, 765.

Microanalysis: C$_{10}$H$_{12}$N$_2$.0.4 H$_2$O: Calc'd: C, 71.74; H, 7.71; N, 16.73. Found: C, 71.74; H, 7.44; N, 16.47.

STEP 3

Imidate

The binitrile (12.5 mmol) was reacted as in the General method Step 3 to give a slightly impure white solid. No further purification was attempted before the next step.

STEP 4

Ester

The imidate (8.6 mmol) was reacted as in the General method Step 4 but the solution was stirred over 5 days. Workup gave a crude solid which was purified by column chromatography (2:1 Heptane:ethyl acetate) to give a clear oil, yield 42%.

$^1$H NMR (CDCl$_3$) 400 MHz: δ 1.10–1.20 (1H, m), 1.27–1.31 (4H, m), 1.31–1.40 (1H, m), 1.40–1.70 (4H, m), 1.85–2.00 (1H, m), 2.20–2.30 (1H, m), 2.37–2.40 (1H, m), 2.50–2.70 (1H, m), 2.70–2.80 (1H, m), 4.21 (2H, q, J=6.8 Hz).

MS (CI) m/z: 107, 153, 162 (100% MH$^+$-C$_2$H$_6$O), 208 (MH$^+$).

IR (Film)$\upsilon_{max}$ cm$^{-1}$: 2963, 2878, 2232, 1736, 1457, 14416, 1372, 1345, 1313, 1193, 1146, 1097, 1030, 948, 868.

Microanalysis: C$_{12}$H$_{17}$NO$_2$: Calc'd: C, 69.54; H, 8.27; N, 6.76. Found: C, 69.40; H, 8.28; N, 6.76.

STEP 5

Lactam

The ester (3 mmol) was hydrogenated as in the General method Step 5 at 30° C., 50 psi for 4 hours. The solution was passed through a pad of Celite, followed by a pad of silica, washing with ethyl acetate. The filtrate was decolourized with charcoal and passed through a second pad of silica. The solvent was removed to give a white solid; yield 67%; mp 100–108° C.

$^1$H NMR (DMSO) 400 MHz: δ 1.00–1.22 (3H, m), 1.33–1.49 (4H, m), 1.50–1.64 (1H, m), 1.85–2.00 (2H, m), 2.17–2.27 (2H, m), 2.92 (1H, d, J=9.3 Hz), 3.10 (1H, d, J=9.5 Hz), 7.45 (1H, Br s).

MS (CI) m/z: 165, 166 (100% MH$^+$), 167.

IR (MeOH) $\upsilon_{max}$ cm$^{31\ 1}$: 3204, 3096, 2945, 2870, 2370, 1682, 1453, 1415, 1372, 1305, 1287.

Microanalysis: C$_{10}$H$_{15}$NO$_2$.0.3 H$_2$O: Calc'd: C, 70.39; H, 9.21; N, 8.21. Found: C, 70.36; H, 8.90; N, 7.93.

STEP 6

Bicyclic[2,2,1] heptane gabapentin

The lactam (1.6 mmol) was reacted as in the General method Step 6 to give an off-white crystalline solid; yield 81%; mp 134–139° C.; [α]$_D$=0 (T=20° C., C=1, MeOH). (Endo:Exo, 3:1).

$^1$H NMR (DMSO) 400 MHz: δ 0.88–0.92 (1H, m), 1.00–1.28 (2H, m), 1.28–1.41 (1H, m), 1.41–1.64 (4H, m), 2.16–2.24 (2H, m), 2.32–2.38 (1H, m), 2.63–2.70 (1H, m), 2.72–2.87 (1H, m), 3.01–3.26 (1H, m), 8.00 (3H, Br s).

MS (CI) m/z: 93, 107, 121, 149, 153, 165, 166 (100% MH$^+$-H$_2$O), 167, 184 (MH$^+$).

IR (MeOH) $\upsilon_{max}$ cm$^{31\ 1}$: 2957, 2361, 1714, 1608, 1506, 1405, 1202.

Microanalysis: C$_{19}$H$_{17}$NO$_2$.1.5 HCl: Calc'd: C, 50.47; H, 7.84; N, 5.89. Found: C, 50.68; H, 8.00; N, 6.00.

Made by similar synthetic methods are the following:

(5) ada (2-Aminomethyl-adamantan-2-yl)-acetic acid;

(1) n=4, m=2 (11-Aminomethyl-bicyclo[4.4.1]undec-11-yl)-acetic acid;

(1) n=2, m=0 (7-Aminomethyl-bicyclo[2.2.1]hept-7-yl)-acetic acid.

We claim:

1. A compound of formula

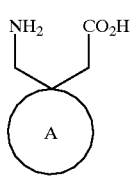

I a pharmaceutically acceptable salt thereof or a prodrug thereof wherein A is a bridged ring selected from

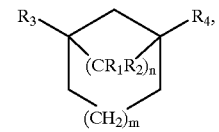
(1)

(2)

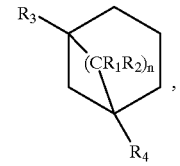
(3)

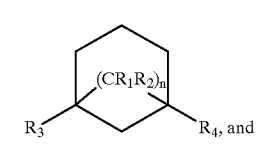
(4)

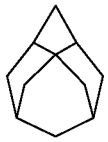
(5)

wherein

R$_1$ and R$_2$ are each independently selected from hydrogen and methyl;

R$_3$ and R$_4$ are each independently selected from hydrogen or methyl;

n is an integer of from 1 to 4; and m is an integer of from 0 to 2.

2. A compound of formula

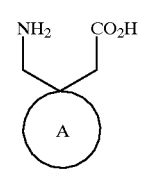

I or a pharmaceutically acceptable salt thereof wherein A is a bridged ring selected from

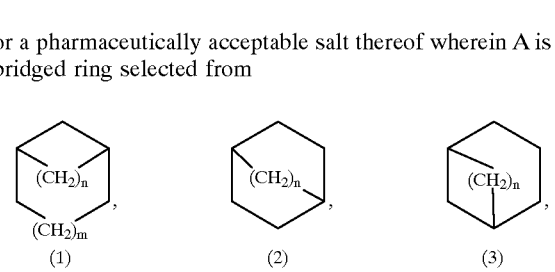
(1)     (2)     (3)

-continued

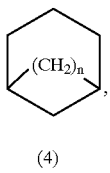

(4)

and

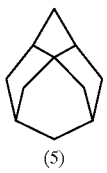

(5)

wherein n is an integer of from 1 to 4; and m is an integer of from 0 to 2.

3. A compound of formula I

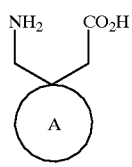

I or a pharmaceutically acceptable salt thereof or a prodrug thereof wherein A is

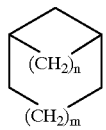

wherein n is an integer of from 1 to 4, and m is an integer of from 0 to 2.

4. A compound according to claim 3 wherein n is 3 and m is 1.

5. A compound according to claim 1 wherein A is

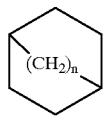

wherein n is an integer of from 1 to 4.

6. A compound according to claim 5 wherein n is 1.

7. A compound of formula I

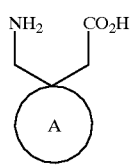

I or a pharmaceutically acceptable salt thereof or a prodrug thereof
wherein A is

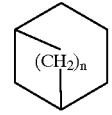

wherein n is an integer of from 1 to 4.

8. A compound according to claim 7 wherein n is 1.

9. A compound of formula I

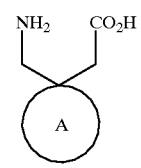

I or a pharmaceutically acceptable salt thereof or a prodrug thereof
wherein A is

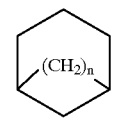

wherein n is an integer of from 1 to 4.

10. A compound according to claim 9 wherein n is 2.

11. A compound of formula I

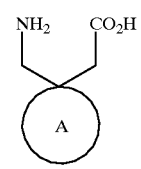

I or a pharmaceutically acceptable salt thereof or a prodrug thereof
wherein A is

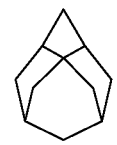

.

12. A compound according to claim 1 selected from
(2-Aminomethyl-bicyclo[2.2.1]hept-2-yl)-acetic acid methyl ester monohydrochloride,
[2-(Acetylamino-methyl)-bicyclo[2.2.1]hept-2-yl]-acetic acid, and
[2-(2-Aminomethyl-bicyclo[2.2.1]hept-2-yl)-acetylamino]-acetic acid monohydrochloride.

13. A pharmaceutical composition comprising a therapeutically effective amount of a compound according to claim 1 and a pharmaceutically acceptable carrier.

14. A method for treating epilepsy comprising administering a therapeutically effective amount of a compound according to claim 1 to a mammal in need of said treatment.

15. A method for treating faintness attacks, hypokinesia, and cranial disorders comprising administering a therapeutically effective amount of a compound according to claim 1 to a mammal in need of said treatment.

16. A method for treating neurodegenerative disorders comprising administering a therapeutically effective amount of a compound according to claim 1 to a mammal in need of said treatment.

17. A method for treating depression comprising administering a therapeutically effective amount of a compound according to claim 1 to a mammal in need of said treatment.

18. A method for treating anxiety comprising administering a therapeutically effective amount of a compound according to claim 1 to a mammal in need of said treatment.

19. A method for treating panic comprising administering a therapeutically effective amount of a compound according to claim 1 to a mammal in need of said treatment.

20. A method for treating pain comprising administering a therapeutically effective amount of a compound according to claim 1 to a mammal in need of said treatment.

21. A method for treating neuropathological disorders comprising administering a therapeutically effective amount of a compound according to claim 1 to a mammal in need of said treatment.

22. A method for treating epilepsy, faintness attacks, hypokinesia, cranial disorders, neurodegenerative disorders, depression, anxiety, panic, pain and neuropathological disorders comprising administering a therapeutically effective amount of a compound of formula

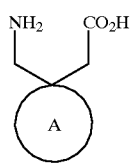

I a pharmaceutically acceptable salt thereof or a prodrug thereof wherein A is a bridged ring selected from

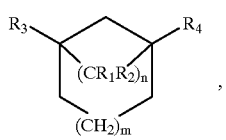

(1)

-continued

(2)

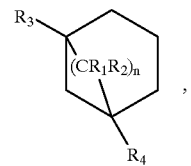

(3)

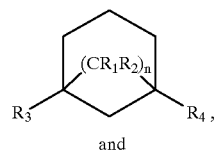

(4)

and

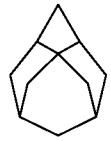

(5)

wherein $R_1$ and $R_2$ are each independently selected from hydrogen and methyl;

$R_3$ and $R_4$ are each independently selected from hydrogen and methyl;

n is an integer of from 1 to 4; and m is an integer of from 0 to 2 to a mammal in need of said treatment.

23. A compound which is 7-aminomethyl-bicyclo[2.2.1]hept-7-yl-acetic acid.

24. A compound which is bicyclic [3.3.1]nonane gabapentin.

* * * * *